US00PP32527P2

(12) United States Plant Patent
Heuger

(10) Patent No.: US PP32,527 P2
(45) Date of Patent: Nov. 24, 2020

(54) ***HELLEBORUS* PLANT NAMED 'COSEH 5100'**

(50) Latin Name: ***Helleborus* x *ericsmithii* x *Helleborus* x *hybridus***
Varietal Denomination: COSEH 5100

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/602,772

(22) Filed: Nov. 29, 2019

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 5100', characterized by its upright and mounded plant habit; moderately vigorous to vigorous growth habit; dark green-colored leaves; freely flowering habit; single light yellow green and red purple to greyed purple bi-colored flowers; and good garden performance.

2 Drawing Sheets

Figure 1:
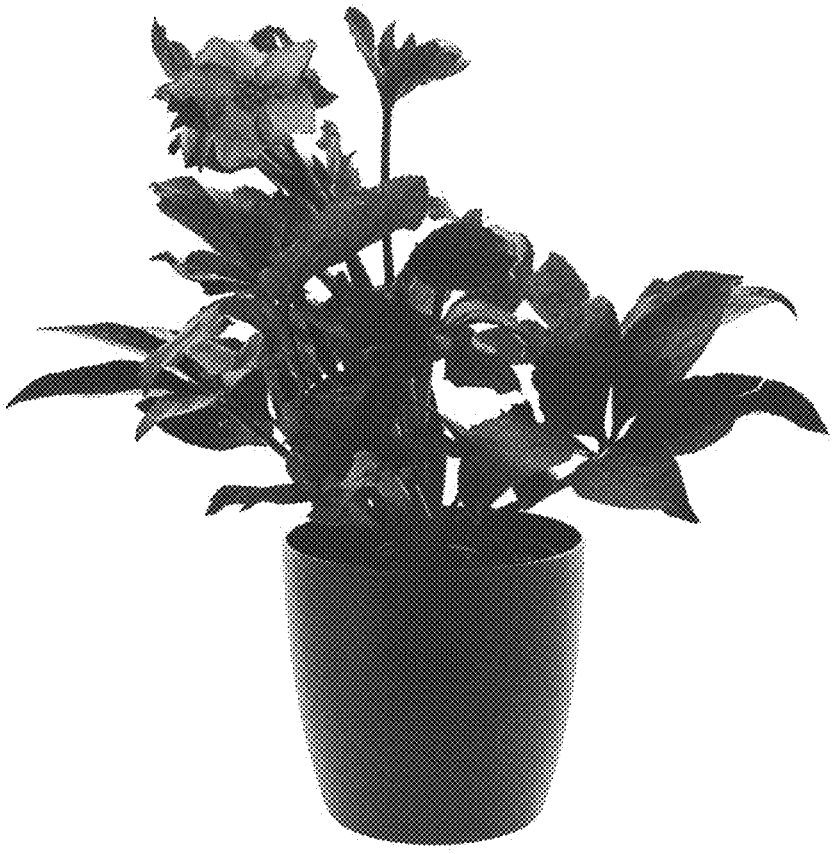

Botanical designation: *Helleborus* x *ericsmithii* x *Helleborus* x *hybridus*.
Cultivar denomination: 'COSEH 5100'.

CROSS-REFERENCED TO CLOSELY-RELATED APPLICATIONS

Title: *Helleborus* Plant Named 'COSEH 5200'
Applicant: Josef Heuger
Filed: Concurrently with the instant application U.S. Plant patent application Ser. No. 16/602,786
Title: *Helleborus* Plant Named 'COSEH 5300'
Applicant: Josef Heuger
Filed: Concurrently with the instant application U.S. Plant patent application Ser. No. 16/602,773
Title: *Helleborus* Plant Named 'COSEH 5400'
Applicant: Josef Heuger
Filed: Concurrently with the instant application U.S. Plant patent application Ser. No. 16/602,736

BACKGROUND OF THE INVENTION

The present invention relates to a new and distinct cultivar of *Helleborus* plant, botanically known as *Helleborus* x *ericsmithii* x *Helleborus* x *hybridus* and hereinafter referred to by the name 'COSEH 5100'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in January, 2012 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in February, 2014.

Asexual reproduction of the new *Helleborus* plant by divisions in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 5100'. These characteristics in combination distinguish 'COSEH 5100' as a new and distinct *Helleborus* plant:

1. Upright and mounded plant habit.
2. Moderately vigorous to vigorous growth habit.
3. Dark green-colored leaves.
4. Freely flowering habit.
5. Single light yellow green and red purple to greyed purple bi-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have light yellow green and red purple to greyed purple bi-colored flowers whereas plants of the female parent selection have cream-colored flowers.

Plants of the new *Helleborus* differ from plants of the male parent selection in the following characteristics:

1. Plants of the new *Helleborus* are taller than plants of the male parent selection.

2. Plants of the new *Helleborus* have fewer and darker green-colored leaves than plants of the male parent selection.

Plants of the new *Helleborus* can be compared to plants of *Helleborus* x *ericsmithii* x *Helleborus* x *hybridus* 'COSEH 5200', disclosed in a U.S. Plant Patent application filed concurrently. Plants of the new *Helleborus* differ primarily from plants of 'COSEH 5200' in flower color as plants of the new *Helleborus* have light yellow green and red purple to greyed purple bi-colored flowers whereas plants of 'COSEH 5200' have purple-colored flowers.

Plants of the new *Helleborus* can be compared to plants of *Helleborus* x *ericsmithii* x *Helleborus* x *hybridus* 'COSEH 5300', disclosed in a U.S. Plant Patent application filed concurrently. Plants of the new *Helleborus* differ primarily from plants of 'COSEH 5300' in flower color as plants of the new *Helleborus* have light yellow green and red purple to greyed purple bi-colored flowers whereas plants of 'COSEH 5300' have purple-colored flowers.

Plants of the new *Helleborus* can be compared to plants of *Helleborus* x *ericsmithii* x *Helleborus* x *hybridus* 'COSEH 5400', disclosed in a U.S. Plant Patent application filed concurrently. Plants of the new *Helleborus* differ primarily from plants of 'COSEH 5400' in flower color as plants of the new *Helleborus* have light yellow green and red purple to greyed purple bi-colored flowers whereas plants of 'COSEH 5400' have white and red purple bi-colored flowers.

Plants of the new *Helleborus* can also be compared to plants of *Helleborus* x *hybridus* 'Anna's Red', disclosed in U.S. Plant Pat. No. 24,720 (known as 'ABCRD02', also known as 'Anna's Red'). In side-by-side comparisons, plants of the new *Helleborus* differ primarily from plants of 'Anna's Red' in the following characteristics:

1. Leaves of plants of the new *Helleborus* have less distinct venation than leaves of plants of 'Anna's Red'.
2. Flowers of plants of the new *Helleborus* are light yellow green and red purple to greyed purple bi-colored whereas flowers of plants of 'Anna's Red' are red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 5100' grown in a container.

Figure 2:
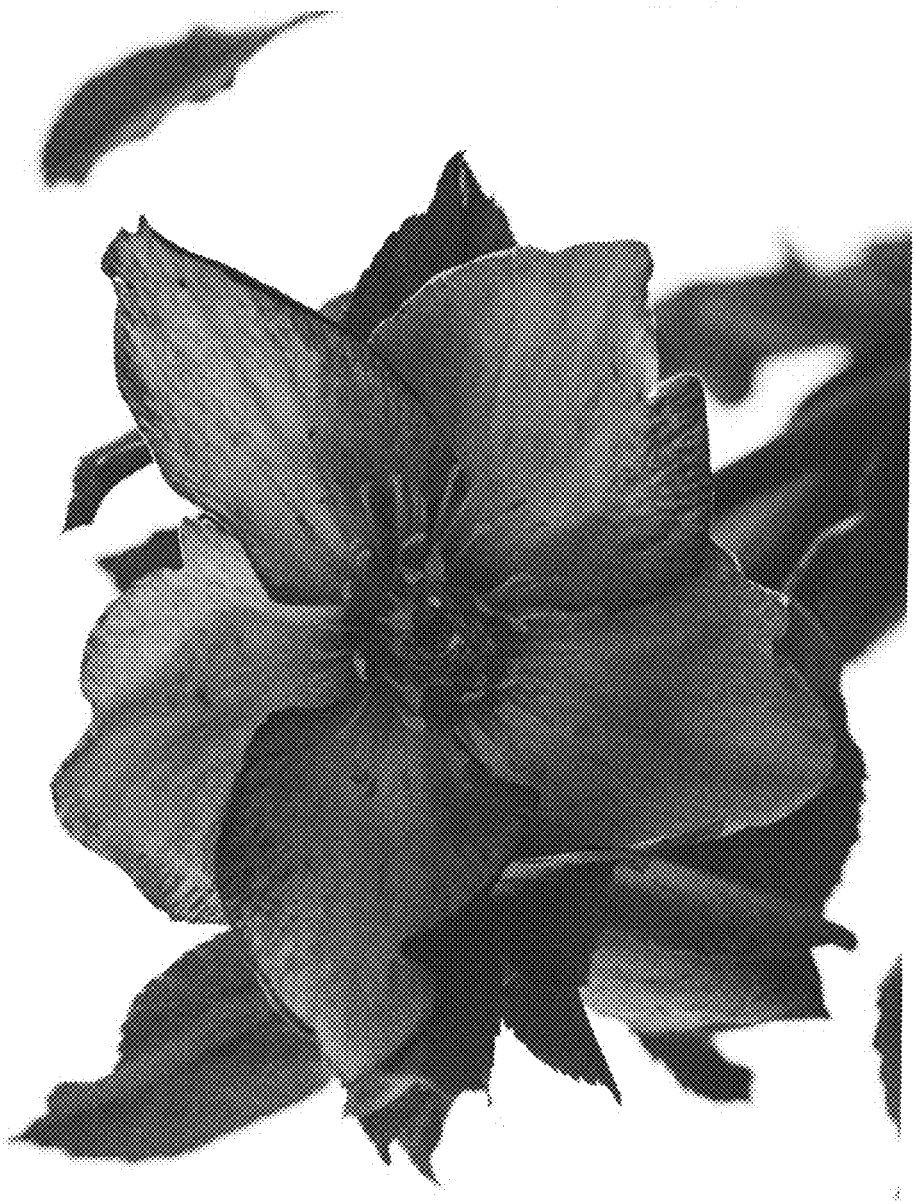

The photograph on the second sheet (FIG. 2 of 2) is a close-up view of typical flowers and leaves of 'COSEH 5100'.

DETAILED BOTANICAL DESCRIPTION

The aforementioned photographs and following observations, measurements and values describe plants grown during December in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* x *Helleborus* x *hybridus* 'COSEH 5100'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, roughly flattened globular to broadly obovate; moderately vigorous to vigorous growth habit and moderate to rapid growth rate.

*Plant height, soil level to top of foliar plane*.—About 27 cm.

*Plant height, soil level to top of flowers*.—About 40.5 cm.

*Plant diameter* (*area of spread*).—About 50.6 cm.

Leaf description:

*Arrangement*.—Leaves arranged in a basal rosette; leaves palmately compound with typically five leaflets per leaf.

*Leaf length*.—About 16.6 cm.

*Leaf width*.—About 20.5 cm.

*Leaflet length*.—About 12.1 cm.

*Leaflet width*.—About 5.4 cm.

*Leaf shape*.—Palmate; reniform in outline.

*Leaflet shape*.—Narrowly ovate to ovate.

*Leaflet apex*.—Acute to narrowly acute.

*Leaflet base*.—Attenuate.

*Leaflet margin*.—Serrate; slightly and coarsely undulate.

*Leaflet texture and luster, upper surface*.—Smooth, glabrous; leathery; slightly to moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 137A. Developing leaflets, lower surface: Close to 147A; midvein, close to 177A. Fully developed leaflets, upper surface: Close to darker than between 147A and N189A; venation, close to 147B. Fully developed leaflets, lower surface: Close to 144A; proximally, close to 200C; venation, close to N199B.

*Petioles*.—Length: About 16.3 cm. Diameter: About 5.5 mm to 7 mm. Strength: Strong. Texture and luster, upper and lower surfaces: Smooth, glabrous; matte to slightly glossy. Color, upper and lower surfaces: Close to 144A; densely covered with fine dots, close to 183C; proximally, dots, close to between N186C and 200B.

Flower description:

*Flower shape and habit*.—Single rotate flowers; flowers slightly to moderately cupped; arranged solitary or in clusters with about twelve flowers each; moderately freely flowering habit with about 25 flowers developing per plant; flowers facing outwardly to slightly nodding.

*Fragrance*.—None detected.

*Natural flowering season*.—Plants begin flowering about ten months after planting; plants flower during the late autumn into the winter in Germany.

*Flower longevity on the plant*.—About ten days; sepals persistent, other flower parts are not persistent.

*Flower buds*.—Length: About 2.2 cm. Diameter: About 1.2 cm. Shape: Ovate. Texture and luster: Smooth, glabrous; matte. Color: Close to 145C; towards the margins, flushed with close to 185C.

*Inflorescence height*.—About 39.8 cm.

*Inflorescence diameter*.—About 19 cm.

*Flower diameter*.—About 7.6 cm by 7.6 cm.

*Flower depth* (*height*).—About 2.5 cm.

*Petals*.—All petals are transformed into nectaries.

*Sepals*.—Quantity and arrangement: About five, arranged in a single whorl. Length: About 4.3 cm. Width: About 3.6 cm. Shape: Broadly ovate, slightly concave. Apex: Obtuse. Base: Truncate to rounded and cuneate. Margin: Entire; not undulate. Texture and luster, upper surface: Smooth, glabrous; matte. Texture and luster, lower surface: Smooth, glabrous; matte to slightly glossy. Color: When opening and fully opened, upper surface: Close to 150D; towards the margins and apex, moderately flushed, marbled and veined with close to 59B to 59C and 187D; with development, close to 144B moderately flushed and marbled with close to 59A. When opening and fully opened, lower surface: Close to 150D; towards the margins and apex, heavily flushed, marbled and veined with close to 60B and 60C; with development, close to 144C and 147D moderately flushed and marbled with close to 59A to 59C.

*Flower bracts*.—Quantity per flower: Typically one or two. Length: About 7.3 cm. Width: About 3.3 cm. Shape: Ovate. Apex: Acute. Base: Truncate. Margin: Serrate; slightly and coarsely undulate. Color, upper surface: Close to 137B; venation, close to 178A. Color, lower surface: Slightly darker than 148A; venation, close to 178A.

*Peduncles*.—Length: About 30.5 cm. Diameter: About 7.5 mm to 9 mm. Aspect: About 10° from vertical. Strength: Strong. Texture and luster: Smooth, glabrous; slightly glossy. Color: Close to 145A; heavily and finely dotted, close to 176B.

*Pedicels*.—Length: About 2 cm. Diameter: About 3 mm. Aspect: About 15° from peduncle axis. Strength: Moderately strong. Texture and luster: Smooth, glabrous; moderately glossy. Color: Close to 145A to 145B; slightly to moderately and finely dotted, close to 182B to 182C.

*Reproductive organs*.—Stamens: Quantity per flower: About 80. Filament length: About 1.6 cm. Filament color: Close to 145D. Anther shape: Double and broadly reniform; basifixed. Anther size: About 2 mm by 2.25 mm. Anther color: Close to 150D. Pollen amount: Scarce. Pollen color: Close to 4D. Pistils: Quantity per flower: About two to four. Pistil length: About 9 mm. Stigma diameter: About 0.3 mm. Stigma shape: Club-shaped. Stigma color: Close to 150D. Style length: About 8 mm. Style color: Close to 182B to 182C; distally, close to 150D. Ovary color: Close to between 145D and 150D. Nectaries (transformed petals): Quantity per flower: About ten. Length: About 1.1 cm. Diameter: About 5 mm. Shape: Tubular, flattened. Texture and luster, inner and outer surfaces: Smooth, glabrous; slightly glossy. Color, immature, inner and outer surfaces: Close to 144C, distally, close to N144B and proximally, close to 144B. Color, mature, inner and outer surfaces: Close to 144C, distally, close to N144B and proximally, close to 144B; with development, close to 144A, distally, close to 153C to 153D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 5100' as illustrated and described.

* * * * *